United States Patent
Ou-Yang et al.

(10) Patent No.: US 10,390,705 B2
(45) Date of Patent: Aug. 27, 2019

(54) PORTABLE NONINVASIVE INSPECTION DEVICE

(71) Applicant: NATIONAL CHIAO TUNG UNIVERSITY, Hsinchu (TW)

(72) Inventors: Mang Ou-Yang, Hsinchu (TW);
Ting-Wei Huang, Taipei (TW);
Chin-Siang Yang, Taichung (TW);
Yao-Fang Hsieh, Taipei (TW);
Sing-Tsung Li, Taichung (TW);
Jin-Chern Chiou, Hsinchu (TW);
Ming-Hsui Tsai, Taichung (TW);
Jeng-Ren Duann, Taichung (TW);
Yung-Jiun Lin, Taichung (TW);
Shuen-De Wu, Taipei (TW); Yung-Jhe Yan, Taipei (TW); Zheng-Lin He, Taichung (TW)

(73) Assignee: National Chiao Tung University, Hsinchu (TW)

(*) Notice: Subject to any disclaimer, the term of this patent is extended or adjusted under 35 U.S.C. 154(b) by 396 days.

(21) Appl. No.: 15/149,632

(22) Filed: May 9, 2016

(65) Prior Publication Data
US 2016/0249809 A1 Sep. 1, 2016

Related U.S. Application Data

(63) Continuation-in-part of application No. 14/066,858, filed on Oct. 30, 2013.

(51) Int. Cl.
*A61B 5/00* (2006.01)
*A61B 1/24* (2006.01)
(Continued)

(52) U.S. Cl.
CPC ........ *A61B 5/0071* (2013.01); *A61B 1/00108* (2013.01); *A61B 1/00186* (2013.01);
(Continued)

(58) Field of Classification Search
CPC ... A61B 1/24; A61B 1/00108; A61B 1/00186; A61B 1/043; A61B 1/063; A61B 1/0646;
(Continued)

(56) References Cited

U.S. PATENT DOCUMENTS 3,890,960 A 6/1975 Wunsch, nee Kuhn et al.
5,055,978 A 10/1991 Rogoff
(Continued)

OTHER PUBLICATIONS

Catherine F. Poh, DDS; Samson P. Ng, DMD, MSc; P. Michele Williams, DMD; Lewei Zhang, DDS, PhD; Denise M. Laronde, RDH, MSc; Pierre Lane, PhD; Calum MacAulay, PhD; Miriam P. Rosin, PhD; "Direct Fluorescence Visualization of Clinically Occult High-Risk Oral Premalignant Disease Using a Simple Hand-Held Device", Wiley InterScience (www.interscience.wiley.com), Sep. 18, 2006.
(Continued)

*Primary Examiner* — Edward Moran
(74) *Attorney, Agent, or Firm* — Rosenberg, Klein & Lee

(57) ABSTRACT

The present invention is directed to a device which includes the following features: a light source illuminates a target to generate an optical inspection signal; a probe head provides an optical path for the optical inspection signal; a probe tube arranged at a front end of the probe head; at least one switched filter module arranged in the optical path, allowing the optical inspection signal to pass therethrough to generate a corresponding spectral signal; and an image sensor arranged behind the switched filter module, receiving the spectral signal and generating a spectral image. The spectral image can be transmitted to an external device, wherefrom the user can use the spectral image to examine the target in further detail. The present invention features a rotary-type or movable-type switched filter module, which facilitates the user to switch filters easily during optical inspection.

17 Claims, 7 Drawing Sheets

(51) Int. Cl.
*A61B 1/06* (2006.01)
*A61B 1/00* (2006.01)
*A61B 1/04* (2006.01)

(52) U.S. Cl.
CPC .............. *A61B 1/043* (2013.01); *A61B 1/063* (2013.01); *A61B 1/0646* (2013.01); *A61B 1/0684* (2013.01); *A61B 1/24* (2013.01); *A61B 5/0084* (2013.01); *A61B 1/00016* (2013.01); *A61B 1/00032* (2013.01)

(58) Field of Classification Search
CPC ....... A61B 1/0684; A61B 1/227; A61B 1/233; A61B 3/0008; A61B 5/0071; A61B 5/0084; A61C 9/0053
USPC .......................................................... 433/29
See application file for complete search history.

(56) References Cited

U.S. PATENT DOCUMENTS

| | | | |
|---|---|---|---|
| 5,946,127 A | 8/1999 | Nagata | |
| 6,110,106 A | 8/2000 | MacKinnon et al. | |
| 6,350,041 B1 | 2/2002 | Tarsa et al. | |
| 6,422,718 B1 | 7/2002 | Anderson et al. | |
| 6,750,971 B2 | 6/2004 | Overbeck et al. | |
| 7,365,844 B2 | 4/2008 | Richards-Kortum et al. | |
| 7,826,728 B2 | 11/2010 | Konno et al. | |
| 8,496,475 B2 * | 7/2013 | Jamnia | H02J 7/0044 433/29 |
| 2005/0003323 A1 | 1/2005 | Katsuda et al. | |
| 2011/0134234 A1 | 6/2011 | Kim | |
| 2013/0034826 A1 | 2/2013 | Walsh et al. | |
| 2015/0118637 A1* | 4/2015 | Ou-Yang | A61B 1/00108 433/29 |

OTHER PUBLICATIONS

Pierre M. Lane, Terence Gilhuly, Peter Whitehead, Haishan Zeng, Catherine F. Poh, Samson Ng, P. Michele Williams, Lewei Zhang, Miriam P. Rosin, Calum E. MacAulay, "Simple Device for the Direct Visualization of Oral-Cavity Tissue Fluorescence", Journal of Biomedical Optics 11(2), 024006 (Mar./Apr. 2006).

Chin-Siang Yang, Mang Ou-Yang, Yao-Fang Hsieh, Yu-Ta Chen, Jin-Chern Chiou, Jeng-Ren Duann, Ming-Hsui Tsai, Shun-De Wu, Cheng-Chung Lee, "Portable Noninvasive System for Oral Cancer Diagnosis", IEEE Conference on Oct. 31, 2012.

Yao-Fang Hsieh, Mang-Ou Yang, Cheng-Chung Lee, "Portable Multispectral Imaging System for Oral Cance Diagnosis", 2013 Optics + Photonics program held between Aug. 25, 2013-Aug. 29, 2013.

* cited by examiner

PORTABLE NONINVASIVE INSPECTION DEVICE

CROSS REFERENCE TO RELATED APPLICATION

This application is a Continuation-in Part of co-pending application Ser. No. 14/066,858, filed on Oct. 30, 2013, currently pending, for which priority is claimed under 35 U.S.C. § 120 and the entire contents of all of which are hereby incorporated by reference.

BACKGROUND OF THE INVENTION

Field of the Invention

The present invention relates to a portable noninvasive inspection device, particularly to a portable noninvasive inspection device, which applies to optical inspection, and whose filters can be switched to meet different requirements.

Description of the Related Art

With advance of inspection technology, there have been various devices for medical inspection in the market. The physicians can diagnose the patents, referring to the inspection results of the inspection devices. The current inspection technology will be described with the exemplification of oral cavity inspection below.

In the current oral cavity inspection technology, the lesion is inspected optically and then biopsied in vivo for microscopic inspection to verify the diagnosis. The conventional oral cavity inspection process is pretty complicated. Further, as the conventional inspection equipment includes a microscope, it is bulky and inconvenient to carry about. Besides, the conventional inspection equipment is invasive to oral tissue and likely to cause physical and psychological discomfort to the testee.

Some handheld devices have been developed to overcome the disadvantages of the conventional inspection devices. For an example, Catherine F. Poh, et al. proposed in Paper 1 "Direct Fluorescence Visualization of Clinically Occult High-Risk Oral Premalignant Disease Using a Simple Hand-Held Device", wherein ultraviolet light is projected onto a target tissue of a testee, and the tester observes the target tissue through a central visualization channel. The prior-art device needs a power cable connected with the device body. Further, the prior-art device cannot store image data but requires the tester to diagnose the target tissue on the spot. For another example, Pierre M. Lane, et al. proposed in Paper 2 "Simple Device for the Direct Visualization of Oral-Cavity Tissue Fluorescence", wherein a special spectrum of light is emitted by a light source and conducted to the handheld device by optical fiber and then projected onto the target tissue by a lens module. For a further example, Nicholas B. MacKinnon proposed in a US patent 2006/6, 110,106A1 a handheld device structure, which is applied to VELscope Vx (a product of the Velscope company), wherein the power supply and the light source are integrated with the handheld device to convenience operation. The prior-art device does not allow the tester to change the filter in the observation channel but still requires the tester to diagnose the target tissue on the spot.

In all the abovementioned conventional inspection devices, the filter is installed in the central visualization channel. In such a scenario, the tester is inconvenient to replace the filter for observing the fluorescent response of the target tissue under a different spectrum of light. Therefore, the present invention proposes a portable noninvasive inspection device to overcome the abovementioned problems.

SUMMARY OF THE INVENTION

The primary objective of the present invention is to provide a portable noninvasive inspection device, wherein a switched filter module cooperates with an image sensor, and wherein the switch-mode filter module enables the tester to switch filters easily during optical inspection, whereby the image sensor can instantly obtain different spectral images of an identical target tissue through different filters.

Another objective of the present invention is to provide a portable noninvasive inspection device, wherein the light source is arranged on the probe head to directly illuminate the target tissue or excite fluorescence from the target tissue, whereby less light energy is consumed in transmission.

To achieve the abovementioned objectives, the present invention proposes a portable noninvasive inspection device, which comprises a light source illuminating a target, such as a lesion, to generate an optical inspection signal; a probe head providing an optical path for the light source to receive the optical inspection signal; at least one switched filter module arranged in the optical path and filtering the optical inspection signal to obtain a corresponding spectral signal; and an image sensor receiving the spectral signal and generating a spectral image.

Another yet objective of the invention is to provide a portable noninvasive inspection device having an inner sleeve and an outer sleeve, in which a light channel is formed between the inner sleeve and the outer sleeve for entering lights of the light source and uniformly distribute lights on the target, so as to avoid the occurrence of abrupt light points and offer sufficient light source for image sensor having a closed surface, thereby providing better imaging quality.

In one embodiment, the switched filter module includes a rotation disc. The rotation disc has a plurality of positioning slots where filters are inserted. The rotation disc is used to switch the filters. The portable noninvasive inspection device further includes a probe tube which is located at a front end of the probe head and having a base at a front end of the probe head. The base includes a mounting seat arranged in its center, in which a light-extracting hole is arranged at the mounting seat and at least one light-entering hole is arranged at an outer side of the mounting seat for receiving lights from the light source. An optical module is arranged on the mounting seat, and an inner sleeve is arranged on the base and annularly telescoped with an outside of the optical module and located at an inner side of the light-entering hole. The inner sleeve has a first opening at its top and a first reflective surface at its outer wall. An outer sleeve is arranged on the base and annularly telescoped with an outside of the inner sleeve and the light-extracting hole, so as to form a light channel with the inner sleeve. The top of the outer sleeve corresponds to the first opening and has a second opening, and the inner wall of the outer sleeve has a second reflective surface. The light of the light source enters the light channel through the light-entering hole and is reflected to the target, so as to reflect the optical inspection signal. The optical inspection signal then enters the optical module through the first opening and the second opening, and finally enters the probe head through the light-extracting hole.

In one embodiment, the switched filter module includes a movable plate. The movable plate has a plurality of positioning slots where filters are inserted. The movable plate is translated to switch the filters. No matter whether the switched filter module has a rotation disc or a movable plate, the filters can be switched manually or automatically.

In one embodiment, the portable noninvasive inspection device of the present invention further comprises a hand-held body accommodating the image sensor and connected with the probe head. A battery module is arranged inside the hand-held body, electrically connected with the light source and the image sensor and supplying power to the light source and the image sensor. A wireless transmission module is also arranged inside the hand-held body, electrically connected with the image sensor and wirelessly transmitting the spectral image to an external device. The design of the built-in battery module and the wireless transmission module greatly increases the convenience and mobility of the present invention in application and operation.

Below, the embodiments are described in detail in cooperation with the attached drawings to make easily understood the objectives, technical contents, characteristics and accomplishments of the present invention.

DETAILED DESCRIPTION OF THE INVENTION

The present invention proposes a portable noninvasive inspection device, which contains a switched filter module and a probe head having an image sensor, wherein a light source is used to illuminate the target tissue and generate an optical inspection signal, and wherein the tester can conveniently select a special filter to filter the optical inspection signal and obtain the filtered image.

Figure 1:
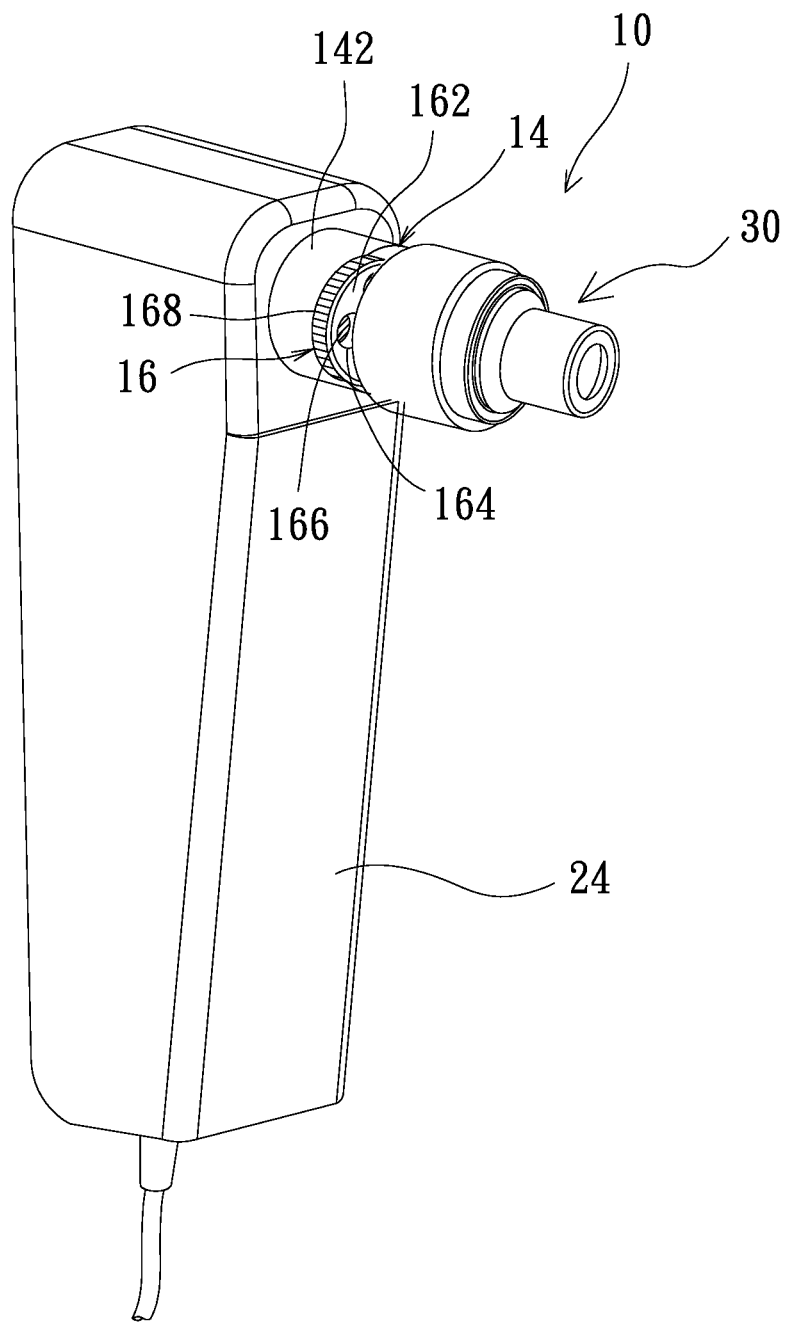
FIG. 1 is a perspective view schematically showing a portable noninvasive inspection device according to a first embodiment of the present invention.
Figure 2:
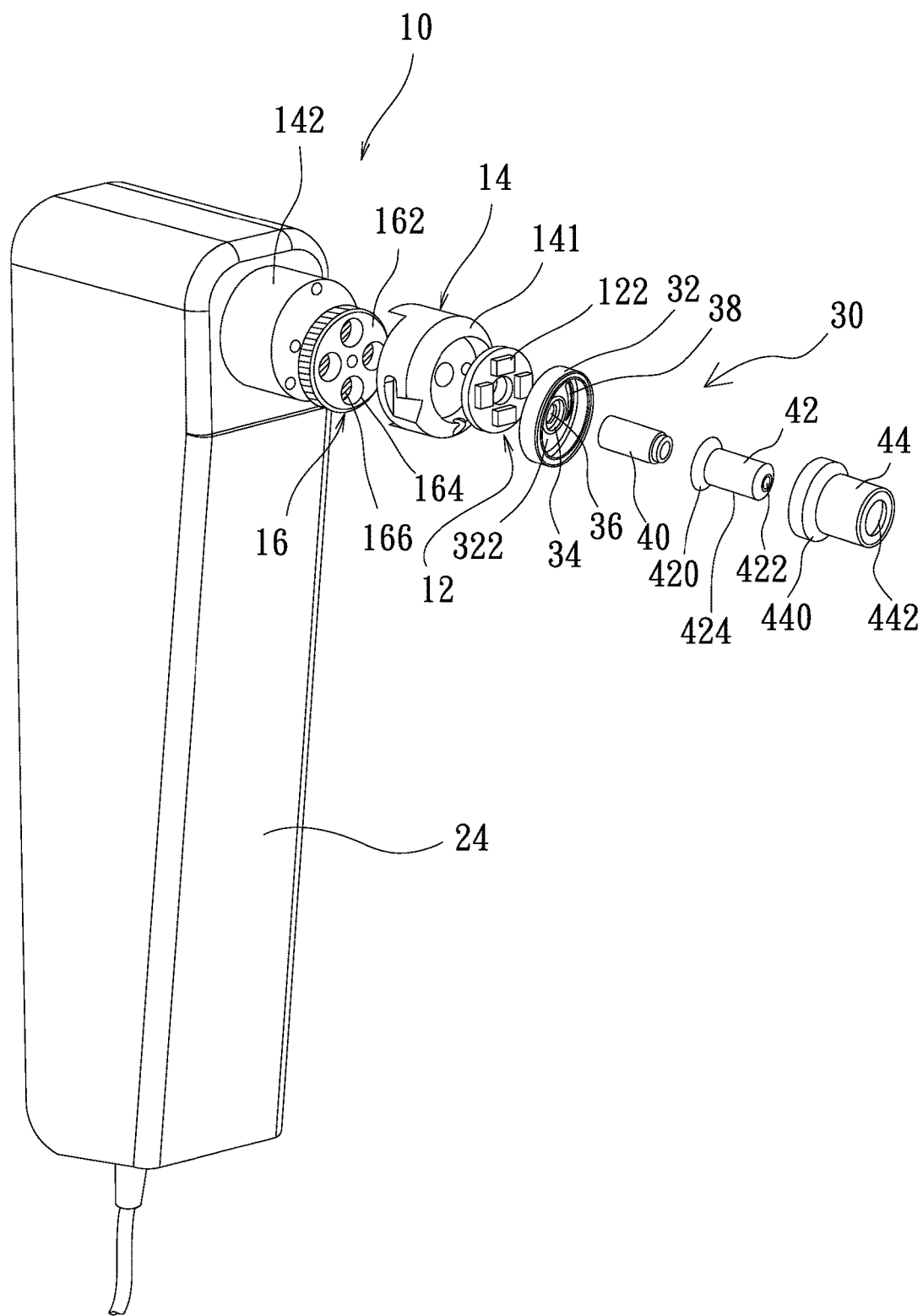
FIG. 2 is an exploded view schematically showing a portable noninvasive inspection device according to the first embodiment of the present invention.
Figure 3:
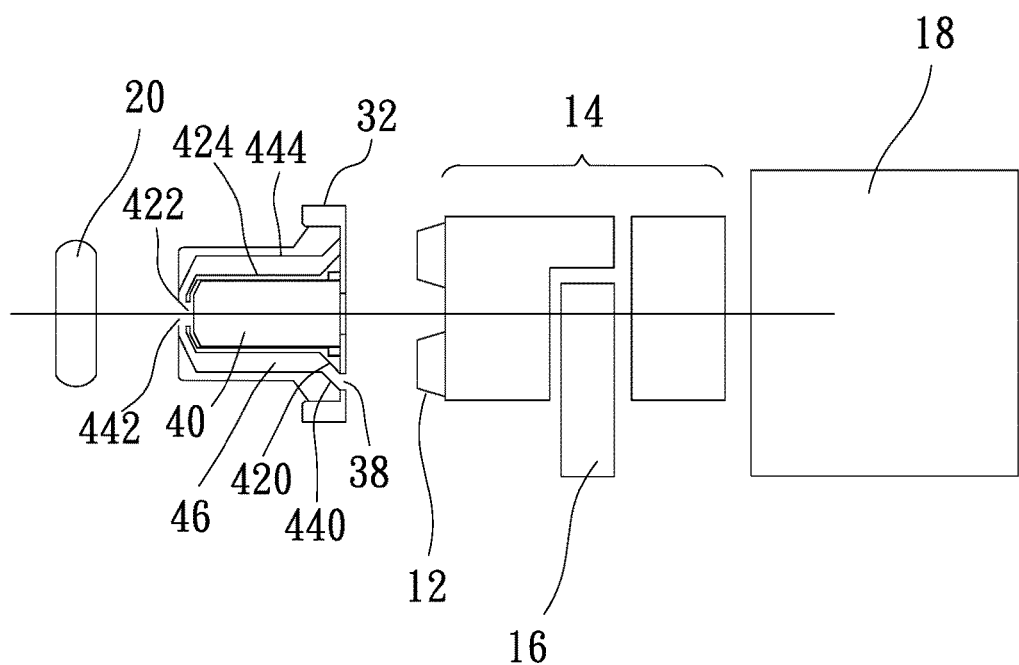
FIG. 3 is a sectional view schematically showing a portable noninvasive inspection device according to the first embodiment of the present invention.

The present invention proposes a portable noninvasive inspection device 10, which comprises a light source 12, a probe head 14, at least one switched filter module 16 and an image sensor 18. The light source 12 is used to illuminate a target 20 to generate an optical inspection signal. In the embodiment shown in FIGS. 1-3, the light source 12 is arranged at the front end of the probe head 14. The probe head 14 provides the light source 12 with an optical path. The probe head 14 receives the optical inspection signal and transmits the optical inspection signal through the optical path. The surface of the probe head 14 is further processed with a sandblasting and blackening process in order to suppress reflections and stray lights. The switched filter module 16 is arranged inside the probe head 14. In the embodiment shown in FIGS. 1-3, the filters are switched via rotation. The switched filter module 16 includes a rotation disc 162 having a plurality of positioning slots 164. Each positioning slot 164 accommodates a filter 166 inserted thereinto. The rotation disc 162 is manually or automatically rotated to switch the filters 166 to make one filter 166 exactly aligned to the optical path. The optical inspection signal travels along the optical path and partially passes through the filter 166. The filter 166 filters the optical inspection signal and obtains a spectral signal. The image sensor 18 is arranged at the rear side of the probe head 14 and the switched filter module 16. The image sensor 18 senses the spectral signal and generates a corresponding spectral image, such as a biomedical image, a fluorescent image or a spectrum-based image. If the light source 12 is a light source for exciting the target 20, the target 20 will be excited to generate a fluorescent optical inspection signal. The fluorescent optical inspection signal is filtered by the switched filter module 16, and the image sensor 18 senses the filtered signal to form a fluorescent image. The portable noninvasive inspection device 10 further comprises a hand-held body 24 accommodates the image sensor 18 and connects with the probe head 14. The hand-held body 24, the probe head 14, and the probe tube 22 cooperate to form a pistol-like handheld device that the user can easily hold and operate.

The portable noninvasive inspection device 10 further includes a probe tube 30 which is arranged at a front end of the probe head 14 and includes a base 32 arranged at a front end of the probe head. The upper surface of the base 32 has a third reflective surface 322, and the center of the base 32 has a mounting seat 34. A light-extracting hole 36 is arranged on the center of the mounting seat 34, and at least one light-entering hole 38 is arranged at an outer side of the mounting seat 34 for receiving light from the light source 12. An optical module 40 is arranged on the mounting seat 34, in which a multiplicity of lens are combined for magnifying the image of the target 20. An inner sleeve 42 is arranged on the mounting seat 34 and annularly telescoped with an outside of the optical module 40 and located at the inner side of the light-entering hole 38. A first reflective ramp 420 is annularly arranged at the bottom of the inner sleeve 42, in which the first reflective ramp 420 is made up of silver and has a slope of 15°-75° with respect to the inner sleeve 42. The inner sleeve 42 further includes a first opening 422 having a diameter of 0.1 mm-10 cm. The outer wall of the inner sleeve 42 includes a first reflective surface 424 which is made up of silver. An outer sleeve 44 is arranged on the base 32 which is annularly telescoped with an outside of the inner sleeve 42 and the light-entering hole 38. The outer sleeve 44 further includes a second reflective ramp 440 arranged at the bottom of the outer sleeve 44, in which the second reflective ramp is made up of silver and has a slope of 15°-75° with respect to the outer sleeve 44. A second opening 442 is arranged at the top of the outer sleeve 44 and corresponds to the first opening 422 of the inner sleeve 42. The inner wall of the outer sleeve 44 has a second reflective surface 444 which is made up of silver. The second reflective surface 444 and the first reflective surface 424 together form a light channel 46. In addition, the surface of the outer sleeve 44 can be further processed with a sandblasting and blackening processing in order to suppress reflections and stray lights.

Figure 4:
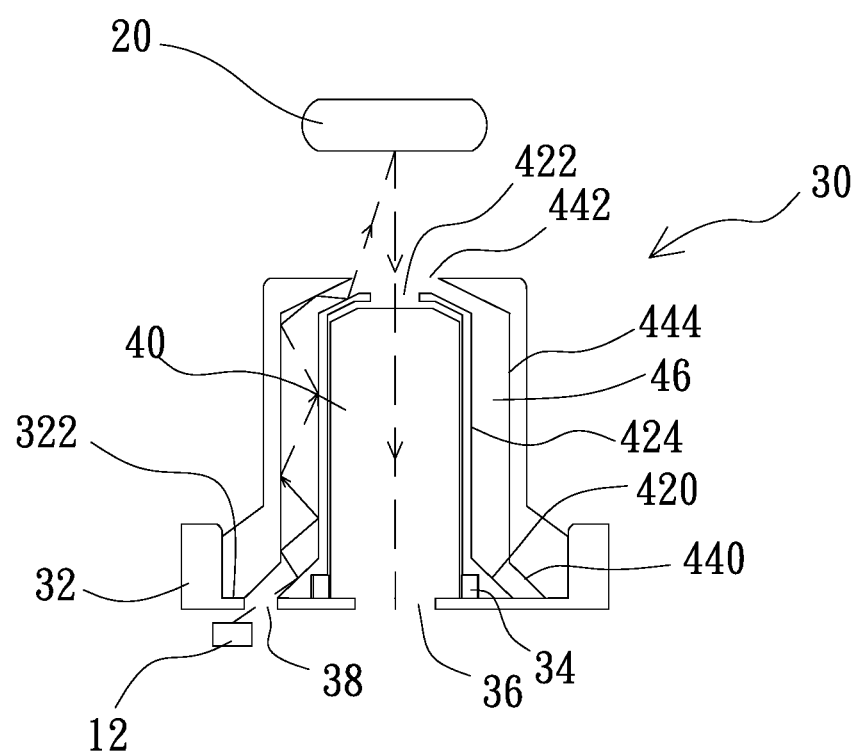
FIG. 4 is a schematic diagram illustrating the light transmission in the probe tube of the present invention.

Next, referring to FIG. 1-FIG. 4, in which FIG. 4 illustrates the usage of the probe tube 30. When the light from the light source 12 enters the light channel 46 through the light-entering hole 38 of the base 32, it projects to the first reflective ramp 420 and the second reflective ramp 440. By the specific slope of the first reflective ramp 420 and the second reflective ramp 440 with the collocation of the reflections of the first reflective surface 424 and the second reflective surface 444, the light is able to be uniformly projected to the target 20 so as to suppress light points having a conspicuously high brightness. In addition, as the upper surface of the base 32 includes a third reflective surface 322, the leaked lights can be refracted back to enhance the intensity of light. After the light is projected to the target 20, the reflective optical inspection signal enters the optical module 40 through the first opening 422 and the second opening 442, in which the optical module 40 functions as magnifier for magnifying the image of the target 20. In this way, the magnified inspection light can enter the probe head 14 so as to be inspected by the image sensor 18.

Figure 5:
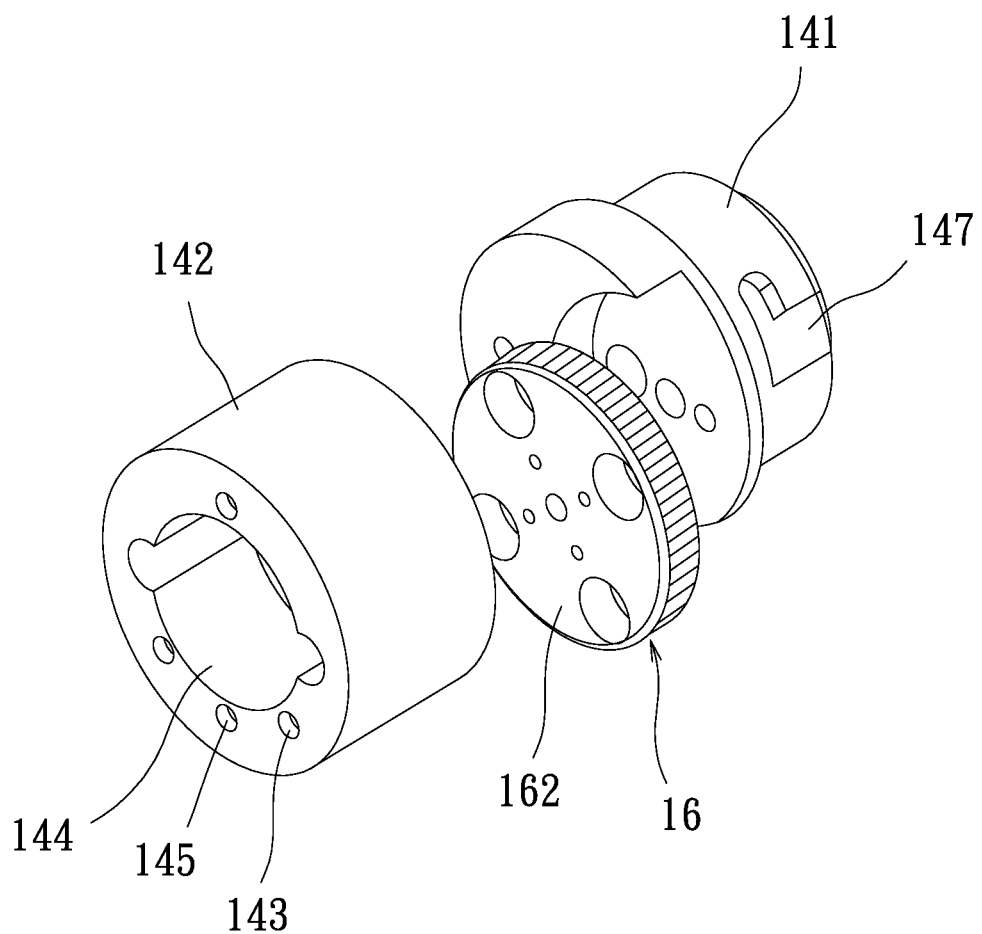
FIG. 5 is an exploded view schematically showing a front probe head structure, a rear probe head structure and a switched filter module of a portable noninvasive inspection device according to the first embodiment of the present invention.

In one embodiment, the light source 12 is realized by at least one LED (Light Emitting Diode) or at least one laser device. In one embodiment, the light source 12 is realized by a plurality of LEDs or laser devices arranged annularly. In the embodiment shown in FIGS. 1-3, the light source 12 is realized by a plurality of LEDs 122 arranged annularly. However, this embodiment is only to exemplify the present invention but not to limit the scope of the present invention. Refer to FIG. 5. The probe head 14 includes a front probe head structure 141 and a rear probe head structure 142. The front probe head structure 141 and the rear probe head structure are assembled together with a space penetrating there through to function as the optical path. The switched filter module 16 is arranged between the front probe head structure 141 and the rear probe head structure 142. The front probe head structure 141, the switched filter module 16 and the rear probe head structure 142 are assembled together to form a sub-system. The rear probe head structure 142 has several holes 143 for fixing the image sensor 18. A circular basin 144 is formed on the rear probe head structure 142 and used as the movement space of an imaging lens (not shown in the drawing) of the image sensor 18. The lower region of the rear probe head structure 142 has a wiring hole 145 where a power cable passes to reach the light source 12 at the front. The rotation disc 162 is eccentric to the central visualization channel, whereby the filter 166 can be aligned to the central visualization channel. The edge of the rotation disc 162 has a grooved rim 168 to convenience finger's swiveling the rotation disc 162. The lower region of the front probe head structure 141 has a wiring hole 146 corresponding to the wiring hole 145 of the rear probe head structure 142. One end of the wiring hole 146 extends to the nearby of the light source 12. Two laterals of the front probe head structure 141 have L-shaped grooves 147. The probe tube 30 is screwed into the L-shape grooves 147 and secured thereto. The front probe head structure 141 and the rear probe head structure 142 have positioning holes, and the positioning beads (not shown in the drawing) are press-fitted into the positioning holes to secure the rotation disc 162. Thus, the filter 166 can be correctly positioned and exactly aligned to the central visualization channel while the tester rotates the rotation disc 162.

The abovementioned embodiments feature the rotary-type switched filter module and the assembly-type probe head structure. The present invention further includes other embodiments, such as the embodiments featuring a movable-type switched filter module and a connection ring, which will be described in detail below. However, the present invention is not limited by the two groups of embodiments.

Figure 6:
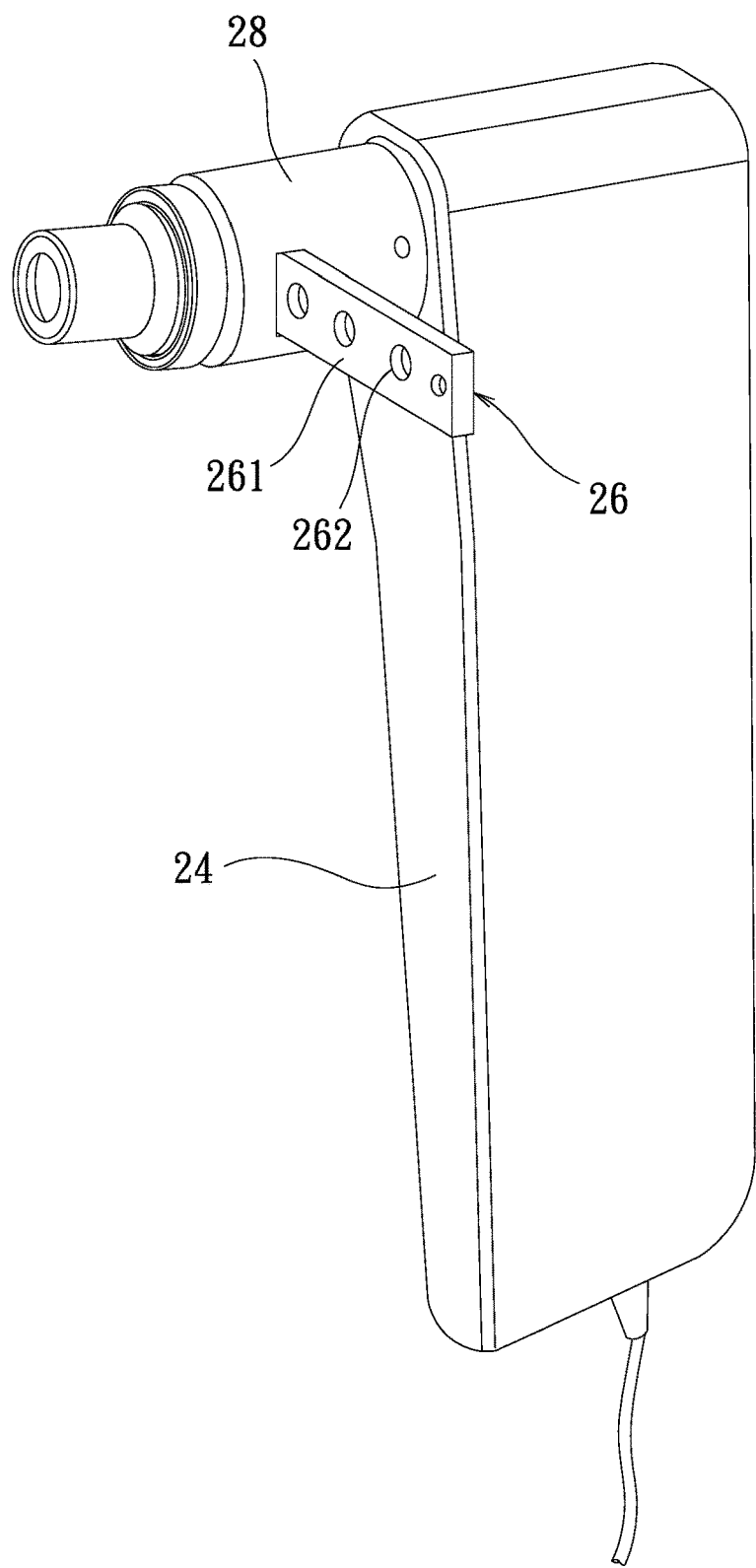
FIG. 6 is a perspective view schematically showing a portable noninvasive inspection device according to a second embodiment of the present invention.
Figure 7:
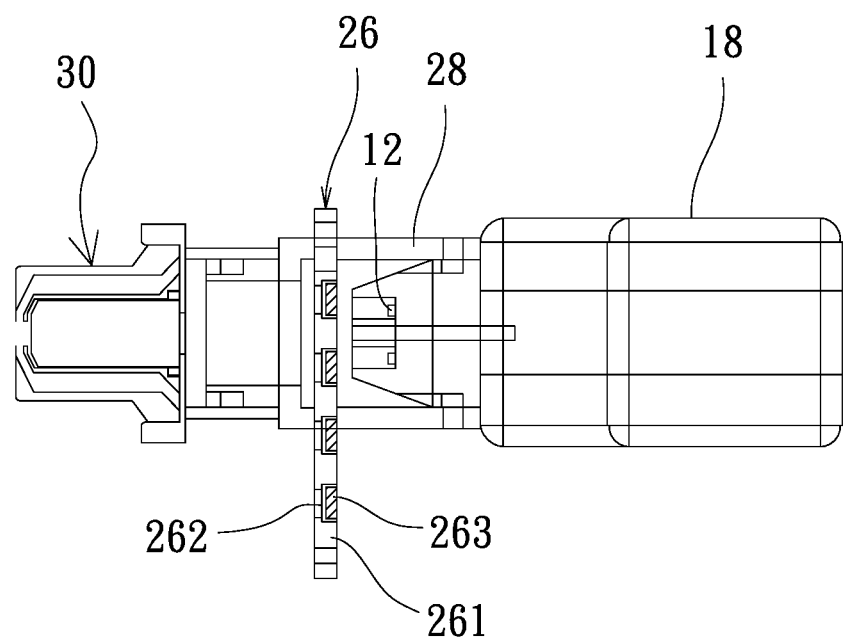
FIG. 7 is an exploded view schematically showing a portable noninvasive inspection device according to the second embodiment of the present invention.

Refer to FIG. 6 and FIG. 7. The movable-type switched filter module 26 further comprises a movable plate 261 inserted into a connection ring 28, which functions as the probe head. The front end of the connection ring 28 is connected with the probe tube 30, and its structure is similar to the structure expounded in the foregoing embodiment. Thus, the details of the structure of the connection ring 28 will not be reiterated here. The rear end of the connection ring 28 is connected with the hand-held body 24, whereby the connection ring 28 joins with the probe tube 30 and the hand-held body 24 to form an integral structure. The light source 12 is arranged inside the connection ring 28, behind the movable-type switched filter module 26, and between the movable-type switched filter module 26 and the image sensor 18. The movable plate 261 has a plurality of positioning slots 262 where a plurality of filters 263 is inserted. The filters 263 are switched via translating the movable plate 261. In one embodiment, the movable plate 261 is made of a transparent material, such as acrylic or glass, lest the light source 12 be shielded by the movable plate 261. The connection ring 28 can be installed between the probe tube 30 and the image sensor 18 without obvious modification.

In the abovementioned embodiments, the light source is arranged before or behind the switched filter module. In some embodiments of the present invention, the light source is arranged before or beside the probe tube, whereby the light source is closer to the target and provides better illumination.

In some embodiments of the present invention, a battery module is built inside the hand-held body, electrically connected with the light source and the image sensor and supplying power to the light source and the image sensor. In some embodiments of the present invention, a wireless communication module is arranged inside the hand-held body, electrically connected with the image sensor and transmitting the spectral images to an external device. The design incorporating the battery module and the wireless communication module contributes convenience and mobility to the present invention in application and operation.

In conclusion, the present invention uses the rotary-type or movable-type switched filter module to switch filters fast and easily during optical inspection, whereby the image sensor can instantly obtain different spectral images of the same target tissue of the target through different filters. The images of the same target tissue, which are obtained through the filters corresponding to different spectral ranges, can be used to analyze the biochemical features of the target tissue. Besides, the light source of the present invention is installed in the probe head, directly illuminating the target tissue or directly exciting the target tissue to generate fluorescence, whereby less light energy is lost in transmission. Also, the light channel between the inner sleeve and the outer sleeve can enter the lights of the light source and uniformly distribute lights on the target, so as to avoid the occurrence of abrupt light points and offer sufficient light for image sensors having a closed surface, thereby providing a better imaging quality.

The embodiments described above are to demonstrate the technical thought and characteristics of the present invention and enable the persons skilled in t art to understand, make, and use the present invention. However, these embodiments are not intended to limit the scope of the present invention. Any equivalent modification or variation according to the spirit of the present invention is to be also included within the scope of the present invention.

What is claimed is:

1. A portable noninvasive inspection device comprising:
   a light source illuminating a target to generate an optical inspection signal;
   a probe head providing an optical path for said optical inspection signal;
   a probe tube arranged at a front portion of said probe head, said probe tube including:
      a base arranged at a front end of said probe head and having a mounting seat at a center thereof, wherein a center of said mounting seat includes a light-extracting hole and an outer side of said mounting seat includes at least one light-entering hole for passing light from said light source therethrough;
      an optical module defining a light passage and including at least one lens, said optical module being arranged on said mounting seat;
      an inner sleeve arranged on said base and coaxially disposed to extend about said optical module, wherein said inner sleeve includes a first opening at a first end thereof and a first reflective surface at an outer wall thereof, said inner sleeve including a first reflective ramp annularly arranged at a second end thereof and angled from said first reflective surface; and
      an outer sleeve arranged on said base and coaxially disposed to extend about said inner sleeve, a light channel being defined between said outer sleeve and said inner sleeve, wherein said outer sleeve includes a second opening located at a first end thereof and corresponds to said first opening, a second reflective surface located at an inner wall of said outer sleeve, said outer sleeve including a second reflective ramp annularly arranged at a second end thereof and angled from said second reflective surface, said light channel being thereby configured to direct light within said light channel toward said second opening and away from said first opening, and light of said light source enters said light channel through said light-entering hole and is projected to said target to generate said optical inspection signal, said optical inspection signal passing through said light passage of said optical module and entering said probe head through said light-extracting hole;
   at least one rotary-type switched filter module arranged in said optical path, said optical inspection signal passing through said rotary-type switched filter module to form a corresponding spectral signal; and
   an image sensor arranged behind said at least one rotary-type switched filter module receiving said spectral signal and generating a spectral image.

2. The portable noninvasive inspection device according to claim 1, wherein said light source contains at least one light emitting diode or laser device.

3. The portable noninvasive inspection device according to claim 2, wherein said light source contains a plurality of light emitting diodes or laser devices arranged annularly.

4. The portable noninvasive inspection device according to claim 1, wherein said rotary-type switched filter module is arranged inside said probe head, and one of a plurality of filters of said switched filter module is exactly aligned to said optical path.

5. The portable noninvasive inspection device according to claim 1, wherein said rotary-type switched filter module includes a rotation disc having a plurality of positioning slots where a plurality of filters are inserted, and said rotation disc is rotated to switch said filters.

6. The portable noninvasive inspection device according to claim 1, wherein a plurality of filters in said switched filter module are switched manually or automatically.

7. The portable noninvasive inspection device according to claim 1, wherein said probe head includes a front probe head structure and a rear probe head structure; said front probe head structure and said rear probe head structure are assembled together with a penetrating space formed thereinside to function as said optical path; said rotary-type switched filter module is arranged between said front probe head structure and said rear probe head structure, and one of a plurality of filters of said rotary-type switched filter module is aligned to said optical path.

8. The portable noninvasive inspection device according to claim 1 further comprising a hand-held body accommodating said image sensor and connected with said probe head.

9. The portable noninvasive inspection device according to claim 8 further comprising a battery module arranged inside said hand-held body, electrically connected with said light source and said image sensor and supplying power to said light source and said image sensor.

10. The portable noninvasive inspection device according to claim 8 further comprising a wireless communication module arranged inside said hand-held body, electrically connected with said image sensor and transmitting said spectral image to an external device.

11. The portable noninvasive inspection device according to claim 1, wherein said light source is arranged before or beside said probe tube.

12. The portable noninvasive inspection device according to claim 1, wherein a surface of said outer sleeve of said probe tube is further processed with a sandblasting and blackening process.

13. The portable noninvasive inspection device according to claim 1, wherein a surface of said probe head is sandblasted and blackened.

14. The portable noninvasive inspection device according to claim 1, wherein said light source is arranged before or behind said rotary-type switched filter module.

15. The portable noninvasive inspection device according to claim 1, wherein said spectral image is a biomedical image, a fluorescent image or a spectrum-based image.

16. The portable noninvasive inspection device according to claim 15, wherein said light source is an exciting light source for said target; said light source excites said target to generate a fluorescent signal as said optical inspection signal; said optical inspection signal is filtered by said rotary-type switched filter module; said image sensor receives said optical inspection signal filtered and generates said fluorescent image.

17. A portable noninvasive inspection device comprising:
   a light source illuminating a target to generate an optical inspection signal;
   a probe head providing an optical path for said optical inspection signal;
   a probe tube arranged at a front portion of said probe head, said probe tube including:
      a base arranged at a front end of said probe head and having a mounting seat at a center thereof, wherein a center of said mounting seat includes a light-extracting hole, an outer side of said mounting seat includes at least one light-entering hole for passing light from said light source therethrough, and an upper surface of said base includes a third reflective surface located at said outer side of said mounting seat;

an optical module defining a light passage and including at least one lens, said optical module being arranged on said mounting seat;

an inner sleeve arranged on said base and coaxially disposed to extend about said optical module, wherein said inner sleeve includes a first opening at a first end thereof and a first reflective surface at an outer wall thereof, said inner sleeve including a first reflective ramp annularly arranged at a second end thereof and angled from said first reflective surface; and an outer sleeve arranged on said base and coaxially disposed to extend about said inner sleeve, a light channel being defined between said outer sleeve and said inner sleeve, wherein said outer sleeve includes a second opening located at a first end thereof and corresponds to said first opening, a second reflective surface located at an inner wall of said outer sleeve, said outer sleeve including a second reflective ramp annularly arranged at a second end thereof and angled from said second reflective surface, said light channel being thereby configured to direct light within said light channel toward said second opening and away from said first opening, and light of said light source enters said light channel through said light-entering hole and is projected to said target to generate said optical inspection signal, said optical inspection signal passing through said light passage of said optical module and entering said probe head through said light-extracting hole;

at least one rotary-type switched filter module arranged in said optical path, said optical inspection signal passing through said rotary-type switched filter module to form a corresponding spectral signal; and an image sensor arranged behind said at least one rotary-type switched filter module receiving said spectral signal and generating a spectral image.

* * * * *